United States Patent [19]

Grambow et al.

[11] Patent Number: 4,914,235

[45] Date of Patent: Apr. 3, 1990

[54] PROCESS FOR OBTAINING GUANIDINE HYDROHALIDES FROM BY-PRODUCT MIXTURES OBTAINED IN THE PRODUCTION OF MERCAPTOALKYLSILANES

[75] Inventors: Clemens Grambow, Seebruck; Ferdinand Beck, Trostberg, both of Fed. Rep. of Germany

[73] Assignee: SKW Trostberg Aktiengesellschaft, Trostberg, Fed. Rep. of Germany

[21] Appl. No.: 320,154

[22] Filed: Mar. 7, 1989

[30] Foreign Application Priority Data

Mar. 16, 1988 [DE] Fed. Rep. of Germany ....... 3808766

[51] Int. Cl.$^4$ .......................................... C07C 129/00
[52] U.S. Cl. .................................................. 564/241
[58] Field of Search ........................................ 564/241

[56] References Cited

U.S. PATENT DOCUMENTS 3,984,471 10/1976 Weinrotter et al. ................. 564/241
4,556,724 12/1985 Seiler et al. .......................... 564/429

FOREIGN PATENT DOCUMENTS 1151254 7/1963 Fed. Rep. of Germany ...... 564/241

*Primary Examiner*—James H. Reamer
*Attorney, Agent, or Firm*—Felfe & Lynch

[57] ABSTRACT

The present invention provides a process for obtaining guanidine hydrohalides from the by-product mixture obtained in the production of mercaptoalkylsilanes and consisting essentially of guanidine hydrohalide, ammonium halide, thiourea and silane compounds, wherein the by-product mixture is extracted with an aliphatic ketone containing up to 7 carbon atoms and the extract is separated from the residue containing the guanidine hydrohalide.

8 Claims, No Drawings

PROCESS FOR OBTAINING GUANIDINE HYDROHALIDES FROM BY-PRODUCT MIXTURES OBTAINED IN THE PRODUCTION OF MERCAPTOALKYLSILANES

The present invention is concerned with a process for obtaining guanidine hydrohalides from the product mixture obtained in the production of mercaptoalkylsilanes.

From Federal Republic of Germany Patent Specification No. 33 46 910, there is known a process for the production of mercaptoalkylsilanes wherein haloalkylsilanes are reacted with thiourea and ammonia. The guanidine hydrohalide, preferably guanidine hydrochloride, thereby obtained as by-product is precipitated by treating the reaction solution with chlorohydrocarbons and subsequently separated, for example, by filtration.

By-products separated in this way contain, on average, only about 65 to 75% by weight of guanidine hydrochloride which is cotaminated with about 5 to 10% by weight ammonium chloride, 5 to 10% by weight thiourea and 10 to 15% by weight silane compounds, as well as 2 to 5% by weight of volatile compounds, for example chlorohydrocarbons and malodorous mercaptans.

Because of the relatively high content of impurities, this by-product is completely unsuitable for the usual fields of use of guanidine salts, for example as synthesis components especially for pharmaceutical products. Because of the good water-solubility and of the ecotoxicological hazards of some of the components, as well as because of the odour, dumping can only take place under strict safety conditions.

Because of the low chemical reactivity of some of the components, as well as of the high nitrogen and chlorine content, burning of this by-product mixture requires a very high expense for additional energy. Furthermore, in the case of burning, large amounts of acidic waste gases, such as hydrogen chloride, sulphur dioxide and nitrogen oxides, are automatically formed.

Therefore, it is an object of the present invention to provide a process for obtaining guanidine hydrohalides from the by-product mixtures obtained in the production of mercaptoalkylsilanes, said mixtures consisting essentially of guanidine hydrohalide, ammonium halide, thiourea and silane compounds.

Thus, according to the present invention, there is provided a process for obtaining guanidine hydrohalides from the by-product mixture obtained in the production of mercaptoalkylsilanes and consisting essentially of guanidine hydrohalide, ammonium halide, thiourea and silane compounds, wherein the by-product mixture is extracted with an aliphatic ketone containing up to 7 carbon atoms and the extract is separated from the residue containing the guanidine hydrohalide.

Surprisingly, we have found that, in this way, guanidine hydrohalides can be obtained in very high purity.

Furthermore, the organic impurities separated from the guanidine hydrochloride are obtained in a form which makes possible a problem-free utilisation or disposal, which was also not foreseeable.

In the process according to the present invention, the by-product mixture which is obtained in the production of mercaptoalkylsilanes, for example, according to Federal Republic of Germany Patent Specification No. 33 46 910 and which, on average, consists of about 65 to 75% by weight guanidine hydrohalide (bromide or chloride), 5 to 10% by weight ammonium bromide or chloride, 5 to 10% by weight thiourea and 10 to 15% by weight silane compounds, as well as 2 to 5% by weight volatile compounds, is subjected to an extraction with an aliphatic ketone which contains up to 7 carbon atoms.

As ketones in the scope of the present invention, there can be used symmetric or asymmetric ketones with aliphatic radicals, which can be saturated or unsaturated, for example methyl, ethyl, vinyl, propyl or isopropyl radicals.

Ketones with 3 or 4 carbon atoms and unbranched radicals are preferred, for example methyl ethyl ketone, methyl vinyl ketone and especially acetone.

The amount of ketone used for the extraction depends essentially upon the weight of the by-product mixture and is preferably the one to two fold amount. The extraction thereby advantageously takes place by digestion of the by-product mixture slurried in the ketone. It is also possible to use larger amounts of ketone but these additional amounts very quickly become uneconomic because the subsequent removal of the solvent thereby causes only unnecessarily high energy costs.

The product mixture slurried in an appropriate ketone is advantageously intermixed by conventional devices. In the course of the extraction, the organic impurities, for example thiourea, dissolve virtually selectively in the ketone, whereas the guanidine hydrohalide and the ammonium halide are left as an insoluble residue.

The extraction can take place not only at ambient temperature but also at an elevated temperature which should, however, be below the boiling point of the ketone used. Preferably, however, working is carried out at ambient temperature.

The extraction can take place in one or more steps, in which case the multi-step extraction can technically very suitably also be carried out as a counterflow extraction.

In a preferred embodiment, the extraction is carried out in two steps, the solution thereby being separated in the usual manner from the solid material after the first extraction step (filtrate I), for example by filtration. Subsequently, the extraction residue is extracted in a second extraction step with fresh solvent and the filtrate II thereby obtained is used again as solvent for the first extraction step of the next batch.

Depending upon the economic requirements, for the achievement of especially high purities of the guanidine hydrohalide, any desired number of further extraction steps can be carried out in an analogous manner.

By means of this technically very simple process, even in two extraction steps, more than 95% of the organic impurities can be removed and a guanidine hyrohalide is obtained with a purity of 90 to 95% which still contains about 5 to 9% by weight of ammonium salts, as well as about 0.3 to 0.8% by weight of impurities (thiourea, silanes and mercaptans).

The ketone extracts obtained in the process according to the present invention, which contain the organic impurities, can also be further worked up by evaporation and recovery of the ketone.

After removal of the ketone solvent, there is obtained a solid material with 35 to 45% by weight thiourea, as well as 40 to 60% by weight of silanes, which can be disposed of in various ways without problems.

The residue obtained from the filtrate by the process according to the present invention can be dumped comparatively favourably. In this way, about 75 to 85% of the dumping room originally required for the by-product can be saved. Furthermore, the dumping of the remaining materials involves smaller risks since the readily water-soluble and corrosive guanidine salts have been largely removed.

A further possibility of disposal of this residue is burning, the amount thereby being reduced by 75 to 85%. Due to the substantial reduction of the nitrogen- and halogen-containing substances, this residual amount also shows more favourable data on specific energy consumption (better calorific value) and substantially lower specific emission or harmful materials, such as nitrogen oxides and hydrogen chloride.

In the case of burning, the recovery of the solvent can also be omitted in order to save a process step and, at the same time, to achieve a higher calorific value (energy saving).

The following Examples are given for the purpose of illustrating the present invention:

EXAMPLE 1.

1 kg. of product mixture, produced according to the process described in Federal Republic of Germany Patent Specification No. 33 46 910 and consisting of 73.4% by weight guanidine hydrochloride, 8.3% by weight thiourea, 12% by weight of silanes and 6.3% by weight ammonium chloride, is slurried in 1 kg. acetone and stirred for 1 hour at 25° C.

The solid material is filtered off (filtrate I), again slurried in 1 kg. acetone, stirred for a few minutes and the end product separated from the filtrate (filtrate II). It is subsequently washed with 200 g. of fresh acetone.

Filtrate I contains about 16% by weight of solid material. After removal of the solvent, there remain 190 g. of solid material with 41% by weight thiourea and 8% by weight guanidine hydrochloride, the remainder being silanes.

Filtrate II contains about 2% by weight of solid material.

The end product (790 g.) is composed of about 91% by weight guanidine hydrochloride, 8% by weight ammonium chloride, 0.3% by weight thiourea and 0.5% by weight of other impurities.

EXAMPLE 2.

1 kg. of product mixture of the same composition as in Example 1 is slurried in 1.1 kg. of filtrate II from Example 1 and stirred at 25° C. for 1 hour. The solid material is filtered off, again slurried with 0.9 kg. acetone (recovered from filtrate I in Example 1), stirred for a few minutes and filtered off. It is subsequently washed with 200 g. of fresh acetone.

The end product (793 g.) is composed of about 91% guanidine hydrochloride, 8% ammonium chloride, 0.4% thiourea and 0.4% of other impurities.

EXAMPLE 3.

300 kg. of product mixture of the same composition as in Example 1 are slurried in 300 kg. acetone and stirred for 1 hour at ambient temperature. The solid material is centrifuged off. There are obtained 224 kg. of crystalline, colourless product containing 0.8% acetone and 0.2% thiourea. The solid material is again slurried in 300 kg. acetone, stirred for 1 hour and centrifuged off, 221 kg. of product being obtained containing 1.3% acetone and 0.03% thiourea.

We claim:

1. The method of recovering a guanidine hydrohalide from the by-product mixtures obtained in the production of mecaptoalkylsilanes, said by-product mixture consisting essentially of guanidine hydrohalide, ammonium chloride, thiourea and silane compounds, with and aliphatic ketone containing up to 7 carbon atoms, and separating the extract from the residue containing the guanidine hydrohalide.

2. The method of claim 1, herein a ketone is used which contains 3 or 4 carbon atoms and unbranched radicals.

3. The method of claim 1, wherein acetone is used as the ketone.

4. The method of claim 1, wherein the extraction is carried out by digestion with a one to two fold amount of ketone, referred to the weight of the by-product mixture.

5. The method of claim 1, wherein the extraction is carried out at ambient temperature.

6. The method of claim 1, wherein the extraction is carried out in several steps.

7. The method of claim 1, wherein the extraction is carried out in counter-current fashion.

8. The method of claim 1, which additionally comprises recovering the ketone after the extraction.

* * * * *

UNITED STATES PATENT AND TRADEMARK OFFICE
CERTIFICATE OF CORRECTION

PATENT NO. : 4,914,235

DATED : April 3, 1990

INVENTOR(S) : Clemens Grambow et al

It is certified that error appears in the above-identified patent and that said Letters Patent is hereby corrected as shown below:

Column 4, line 29, after "compounds," insert --which comprises extracting the by-product mixture--.

Column 4, line 29, "and" second occurrence should read --an--.

Signed and Sealed this

Twenty-sixth Day of November, 1991

Attest:

HARRY F. MANBECK, JR.

*Attesting Officer*  *Commissioner of Patents and Trademarks*